United States Patent
Hoagland

[11] Patent Number: 6,128,950
[45] Date of Patent: Oct. 10, 2000

[54] SPRING TESTING CONTAINMENT

[75] Inventor: Robert C. Hoagland, Citrus Heights, Calif.

[73] Assignee: The United States of America as represented by the Secretary of the Air Force, Washington, D.C.

[21] Appl. No.: 08/910,059

[22] Filed: Aug. 12, 1997

[51] Int. Cl.$^7$ ................................ G01L 1/04; G01N 3/26
[52] U.S. Cl. ................................ 73/161; 73/818
[58] Field of Search ................................ 73/161, 813, 818

[56] References Cited

U.S. PATENT DOCUMENTS

| 1,650,736 | 11/1927 | Zelov | 73/161 |
| 2,164,453 | 7/1939 | Gaskins | 73/161 |
| 2,559,400 | 7/1951 | Clark | 73/161 |
| 3,834,228 | 9/1974 | Wachholz | 73/161 |

Primary Examiner—Hezron Williams
Assistant Examiner—Willie Morris Worth
Attorney, Agent, or Firm—William G. Auton

[57] ABSTRACT

A device which can be used to test heavy coil springs, which is of simple low-cost construction, but which is so designed that the spring can be readily mounted thereon for testing and can be readily removed when testing is completed, and will effectively retain the spring in proper position during testing, using: two containment plates, a cage made of 5 rods that pass through equi-distributed holes in the plates to contain a spring under test, and a central push rod which passes through the center of the assembly to move the containment plates together or apart as required to test the spring. A conventional spring test gauge may be fixed to either the push rod of one of the containment plates to measure the pressure generated by the spring during the test. The containment rods form a cage that expands as the containment plates compress the spring to permit the testing of long springs, and for safe testing of all springs.

1 Claim, 3 Drawing Sheets

SPRING TESTING CONTAINMENT

STATEMENT OF GOVERNMENT INTEREST

The invention described herein may be manufactured and used by or for the Government for governmental purposes without the payment of any royalty thereon.

BACKGROUND OF THE INVENTION

The invention relates generally to spring test systems, and more specifically, it relates to a new kind of spring containment system that is test integral to the spring test system Various types of coil spring testing devices have been provided in the past but usually have been designed for testing light valve springs and not for testing heavy coil springs of the type commonly used in car-suspension systems, such as those used in suspension systems for racing cars. These devices have usually been complicated and expensive, and have been of such a nature that mounting the spring to be tested is difficult and have not effectively held the spring during testing.

The present invention provides a device which can be used to test heavy coil springs, which is of simple low-cost construction, but which is so designed that the spring can be readily mounted thereon for testing and can be readily removed when testing is completed, and will effectively retain the spring in proper position during testing. Furthermore, the device can be readily actuated to give a quick accurate reading on the strength of the spring. Also, the device can be ruggedly constructed and of compact configuration for convenience of handling and portability.

The task of providing spring containment and testing systems is alleviated by the following U.S. Patents, the disclosures of which are incorporated herein by reference:

U.S. Pat. No. 4,186,594, Feb. 5, 1980, Portable spring tester, Mitchell, William E U.S. Pat. No. 4,175,431, Nov. 27, 1979, Heavy duty spring testing apparatus and method, DeTournay, Henry R., U.S. Pat. No. 4,157,033, Jun. 5, 1979, Spring tester, Shereda, Daniel J., U.S. Pat. No. 3,834,228, Sep. 10, 1974, COIL SPRING TESTING DEVICE, Wachholz, U.S. Pat. No. 3,808,885, May 7, 1974, SPRING TESTER, Carlson, Harold C. R., U.S. Pat. No. 3,675,479, Jul. 11, 1972, SPRING TESTER, Carlson, Harold C. R., and U.S. Pat. No. 3,640,129, Feb. 8, 1972, VALVE SPRING TESTER, Bandimere, John C.

The above-cited references disclose alternative spring testing systems that can be simplified or improved by the present invention.

SUMMARY OF THE INVENTION

The present invention provides a device which can be used to test heavy coil springs, which is of simple low-cost construction, but which is so designed that the spring can be readily mounted thereon for testing and can be readily removed when testing is completed, and will effectively retain the spring in proper position during testing, using: two containment plates, a cage made of 5 rods that pass through equi-distributed holes in the plates to contain a spring under test, and a central push rod which passes through the center of the assembly to move the containment plates togeather or apart as required to test the spring. A conventional spring test gauge may be fixed to either the push rod of one of the containment plates to measure the pressure generated by the spring during the test.

It is an object of the present invention to provide safety and secutity of people testing springs.

It is another object of the invention to provide a new kind of spring containment system that is adjustable for different sizes of springs.

These objects will become clearer in view of the description provided below.

DESCRIPTION OF THE PREFERRED EMBODIMENT

Figure 1:
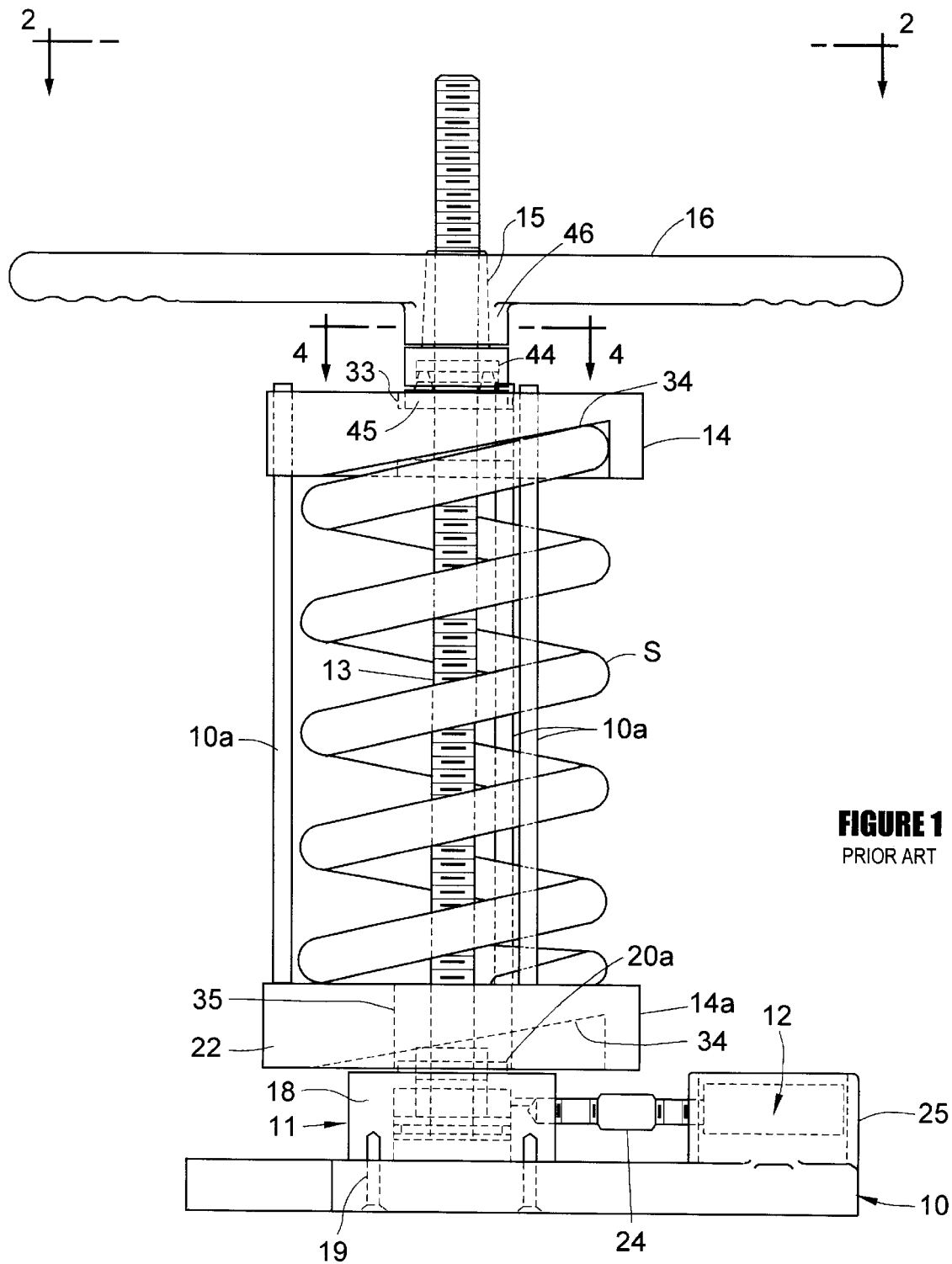
FIG. 1 is a side elevational view of a prior art spring testing device

Referring to FIG. 1 of the drawings, there is shown a pictorial representation of the basic elements of a prior art spring testing, which lacks a containment system to prevent the spring under test from escapint out to one side during testion. Since the present invention is an improvement that uses all of the elements of this prior art system, the prior art system needs to be explained.

FIG. 1 is a side elevational view of the spring testing device with a spring in place to be tested. The device is shown generally as comprising a base 10, a hydraulic load cell 11 and connected indicator gauge 12 carried at the upper side thereof, a vertically disposed screw 13 upstanding from the load cell and operatively connected thereto, an upper spring retainer 14 and a lower spring retainer 14a to be mounted on the screw 13 above and below the spring S to be axially movable relative to the screw S, a nut 15 threaded on the upper end of the screw for engaging with the upper retainer 14, and a turning handle 16 removably mounted on the nut.

The base 10 may be of metal and of suitable spider-like form being shown with the three radially extending legs 10a which are equally angularly spaced. Two of the legs may have friction pads 17 on their upper surfaces adjacent their outer ends to be engaged by the toes of a person using the device to hold it firmly on the floor. The remaining leg has the gauge 12 supported thereon at its outer end. This gauge may be any suitable hydraulically actuated type.

The load cell 11 consists of a cylinder 18 which is mounted centrally on the base 10 and is secured in place by the bolts 19 extending upwardly through the base. The upper end of the cylinder is provided with an inwardly extending flange 20 which carries an O-ring in engagement with the upward tubular extension 21 forming part of a piston 22, which also carries an O-ring that engages the interior of the cylinder 18. Flange 20 is provided with an upwardly projecting central annular lip 20a. Thus, an annular chamber 23, containing hydraulic fluid, is provided in the upper part of the cylinder 18 above the piston 22. This chamber is connected through a tube 24 to the housing 25 of the gauge 12. Thus, upward movement of the piston 22 in the cylinder 18 will actuate the gauge 25.

The screw 13 is of considerable extent and is disposed vertically being connected at its lower end to the piston 22. This is preferably accomplished by passing the lower end of the screw through the extension 21 and piston 22 and fixing its lower end thereon to prevent relative axial movement, such as by staking at its lower extremity as indicated at 26.

As indicated, for mounting the spring S on the screw 13, an upper spring retainer 14 and a lower spring retainer 14a are used. Each of these retainers is reversible so that it can be used with either face in contact with the associated spring end which in some instances is flat and others is helical. Each retainer is in the form of a relatively thick disc which has a radial slot 30 extending thereinto with a slightly enlarged semi-circular socket 31 at its inner end to enclose the screw but permit relative axial movement. The one face of the upper retainer is indicated as having an annular flat surface 32, against which the straight end of the spring may engage and which surrounds a recessed central socket 33.

The prior art system of FIG. 1 has many variations in the art, and include a use of hydraulic, electrical and mechanical acutators and gauges to compress and measure spring performance. Examples of such modern machines are the Tinius Olsen Universal testing machine, and other spring testers of the Link Engineering Co. of Detroit, Mich. Such systems are excellent, but they can be improved by the present invention, which adds a spring containment system to prevent an escape of the spring under test. The present invention can use all the elements of such prior art systems, including the many spring gauge variations that are in use.

Figure 2:
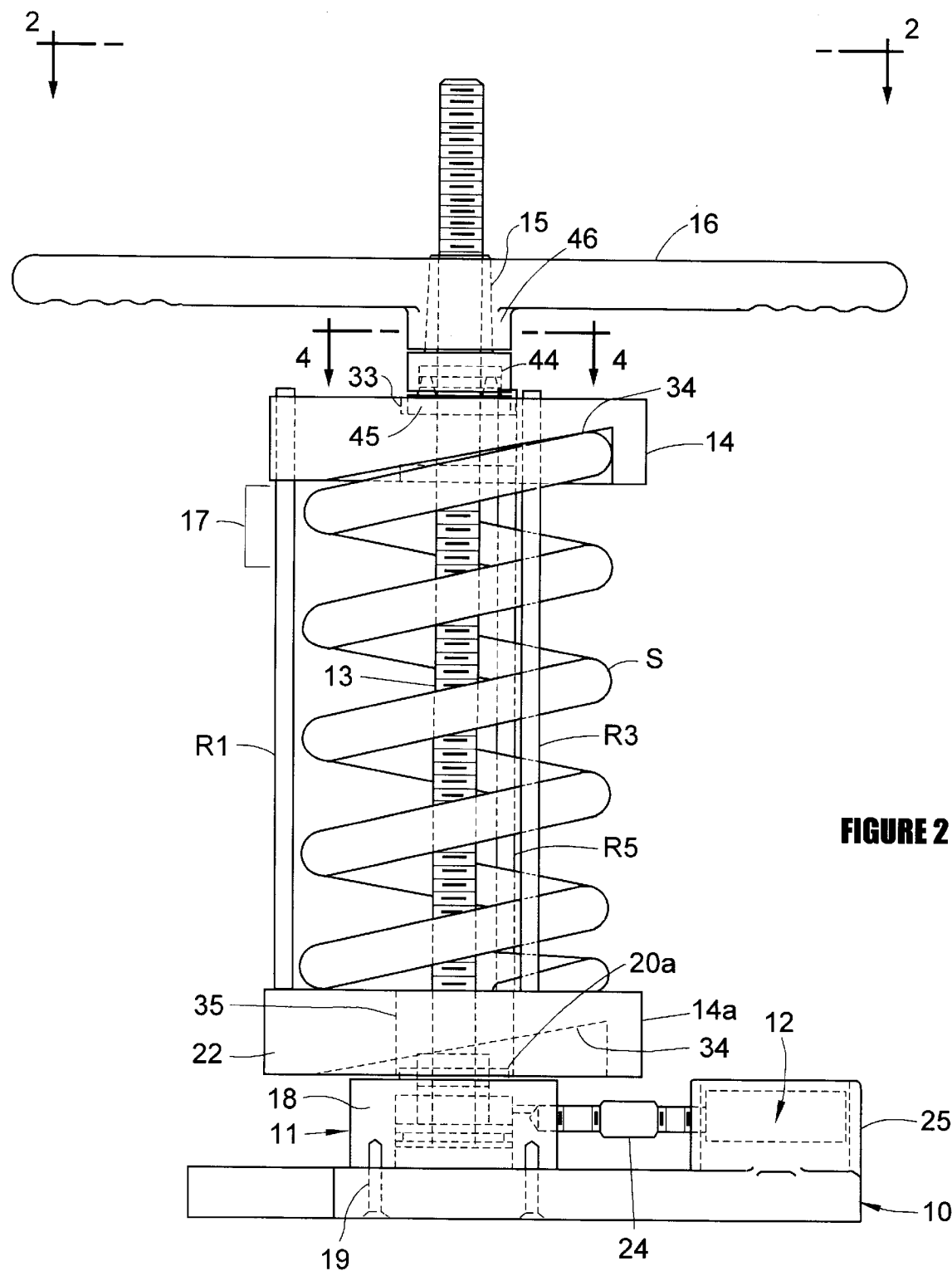
FIGS. 2 illustrates the system of FIG. 1 with the spring containment system of the present invention added.
Figure 3:
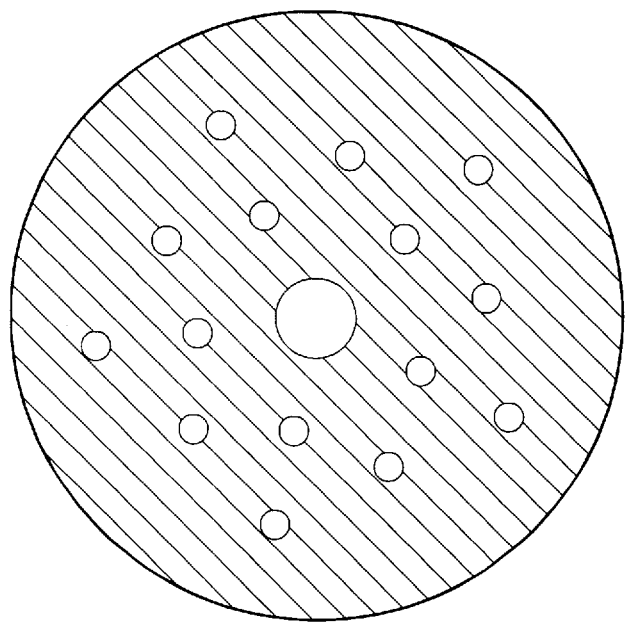
FIG. 3 illustrates an example of an upper or lower compression plate.

FIGS. 2–3 illustrate the spring containment system of the present invention as added to the system of FIG. 1. This system adds five rods to form a containment cage that passes through the upper and lower compression plates in a manner that surrounds the spring and keeps it from escaping out the sides during testing. The number of rods can be varried, but they should be placed in a pattern of equi-distribution around the circumference of the spring.

FIG. 3 shows a plate that can be either the upper or lower compression plate to illustrate a second feature of the invention.: adjustability. When the upper and lower plates contain several sets of accomodation holes for the containment rods, the rods may form cages with different diameters to permit the testing and containment of different diameters of springs. The rods will all be bolted to the base of the nonmoving compression plate, and will slide and pass through the holes in the moving compression plate. Accordingly, the holes in the moving compression plate should be large in diameter in comparison with the containment rods, or even lubricated so that the containment system has no impact on the test readings of the spring. The multiple containment rods are put around the spring to form a cage that has adjustable dimensions and a diameter that will be varied as the different sets of holes have different diameters of distance from the center of the plate.

Figure 4:
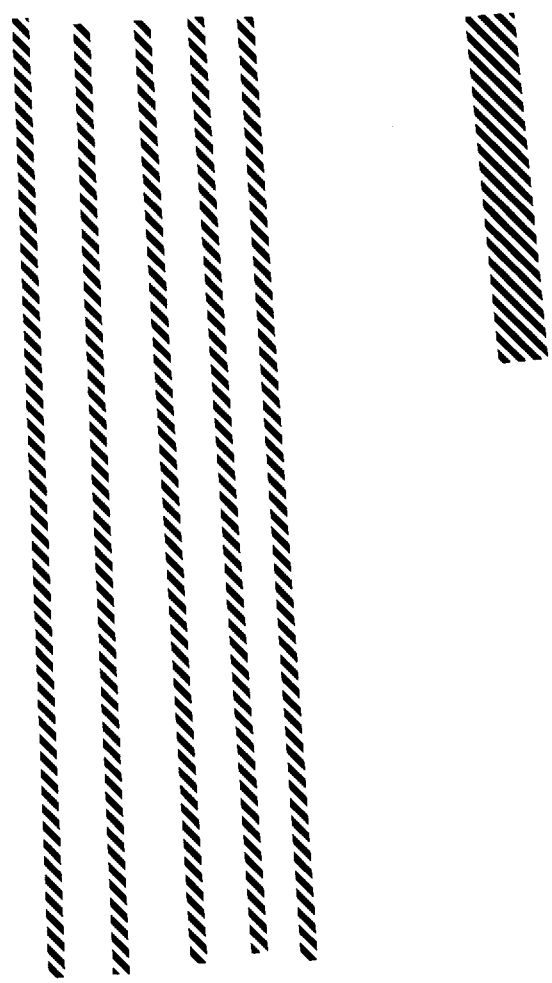
FIG. 4 shows the five containment rods and push rod used with the FIG. 4 compression plate.

FIG. 4 shows the five containment rods and push rod used with the FIG. 4 compression plate. The material, length and thickness of each rod will be selected based upon the nature of the spring being tested. A typical spring tester device can test springs at pressures of from zero to 500 pounds, for an initial spring length of 18 inches and spring diameter of 1.50 inches. The containment rods facilitate the testing of relatively long springs, with lengths of 42 inches or more. As an alternative approach, the push rod can extend through the center of the spring under test, and be screwed into the moveable compression plate to move it, instead of the prior art approach.

The present invention may also be considered a process of improving existing sprint tester systems, such that the process includes a step of adding an adjustable containment system about the spring under test, where the containment system is as described above.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A spring testing system comprising:

first and second compression plates each having a pattern of sets of holes, wherein the holes in each set of holes in the first and second compression plate are distributed such that the holes of each respective set of holes in the first compression plate are equi-distributed around a center point on the first compression plate and aligned with a corresponding hole on the second compression plate, and wherein all holes in a first set have a first uniform distance from the center on the first compression plate, and wherein all holes in a second set have a second uniform distance from the center on the first compression plate, wherein the second uniform distance is larger than the first uniform distance;

a set of containment rods which pass through the sets of holes in the first and second compression plates to form cage having adjustable dimensions to surround a spring under test and prevent its escape during testing, wherein said set of containment rods comprise five containment rods that are equi-distributed about the spring, wherein the containment rods are fixed to the first compression plate, and pass through the holes in the second compression plate, a means to secure the containment rods; a means for compressing the compression plates; and a means for measuring the performance of the spring under test.

* * * * *